United States Patent
Xu et al.

(10) Patent No.: US 8,778,312 B2
(45) Date of Patent: Jul. 15, 2014

(54) DENSENSITIZING DENTIFRICE EXHIBITING DENTAL TISSUE ANTIBACTERIAL AGENT UPTAKE

(75) Inventors: Guofeng Xu, Plainsboro, NJ (US); Ravi Subramanyam, Belle Mead, NJ (US)

(73) Assignee: Colgate-Palmolive Company, New York, NY (US)

( * ) Notice: Subject to any disclaimer, the term of this patent is extended or adjusted under 35 U.S.C. 154(b) by 93 days.

(21) Appl. No.: 13/260,799

(22) PCT Filed: Apr. 1, 2009

(86) PCT No.: PCT/US2009/039194
§ 371 (c)(1),
(2), (4) Date: Sep. 28, 2011

(87) PCT Pub. No.: WO2010/114538
PCT Pub. Date: Oct. 7, 2010

(65) Prior Publication Data
US 2012/0020900 A1    Jan. 26, 2012

(51) Int. Cl.
| A61K 8/46 | (2006.01) |
| A61K 8/18 | (2006.01) |
| A61K 8/33 | (2006.01) |
| A61K 8/34 | (2006.01) |
| A61K 8/20 | (2006.01) |
| A61K 8/19 | (2006.01) |
| A61Q 11/00 | (2006.01) |

(52) U.S. Cl.
USPC ............................................. 424/56; 424/49

(58) Field of Classification Search
None
See application file for complete search history.

(56) References Cited

U.S. PATENT DOCUMENTS

| 4,824,661 A | | 4/1989 | Wagner |
| 4,894,220 A | | 1/1990 | Nabi et al. |
| 4,898,690 A | * | 2/1990 | Bitter et al. ................... 510/135 |
| 5,037,635 A | | 8/1991 | Nabi et al. |
| 5,156,835 A | | 10/1992 | Nabi et al. |
| 5,188,821 A | | 2/1993 | Gaffar et al. |
| 5,192,531 A | | 3/1993 | Gaffar et al. |
| 5,288,480 A | | 2/1994 | Gaffar et al. |
| 5,316,758 A | | 5/1994 | Morishima et al. |
| 5,344,641 A | | 9/1994 | Gaffar et al. |
| 5,453,265 A | | 9/1995 | Gaffar et al. |
| 5,531,982 A | | 7/1996 | Gaffar et al. |
| 5,538,715 A | | 7/1996 | Gaffar et al. |
| 5,599,526 A | | 2/1997 | Viscio et al. |
| 5,723,105 A | * | 3/1998 | Viscio et al. ................... 424/49 |
| 6,096,293 A | * | 8/2000 | Stringer et al. ................ 424/49 |
| 6,692,726 B1 | * | 2/2004 | Morgan et al. ................. 424/50 |
| 6,776,435 B2 | | 8/2004 | Foo et al. |
| 7,153,493 B2 | | 12/2006 | Nelson et al. |
| 2006/0204453 A1 | | 9/2006 | Giniger |
| 2007/0014740 A1 | | 1/2007 | Miller et al. |

FOREIGN PATENT DOCUMENTS

| CN | 1720022 | 1/2006 | |
| EP | 0161898 | 11/1985 | |
| EP | 0278744 | * 8/1988 | ............... A61K 7/16 |
| EP | 0324719 | 7/1989 | |
| EP | 1040819 | 10/2000 | |
| GB | 2413493 | 11/2005 | |
| JP | 2005-068071 | 3/2005 | |
| RU | 2183453 | 6/2002 | |
| WO | WO 00/066070 | 11/2000 | |
| WO | WO 00/66070 | * 11/2000 | |
| WO | WO 2007/069429 | 6/2007 | |

OTHER PUBLICATIONS

Texapn N70 MSDS in www.cospha.ro/dbimg/Texapon%20N%2070.pdf.*
Texapon Product Data Sheet at www.cospha.ro.dbimg/Texapon%20N%2070.pdf (retrieved from the internet on Apr. 4, 2013).*
Di-potassium monohydrogen phosphate in www.chemspider.com/Chemical-Structure. 22858.html (retrieved from the internet Jul. 9, 2013).*
"Texapon N70 MSDS" in www.cospha.ro/dbimg/Texapon%20N%2070.pdf (retrieved from the internet on Apr. 4, 2013).*
Bang, 2008, "Foaming Dentifrice Composition with Antimicrobial Effects," Chemical Abstracts Service database, KR2008006109, Accession No. 2008:214155.
International Search Report and Written Opinion in International Application No. PCT/US09/039194 mailed Jan. 7, 2010.
Nabi et al., 1989, "In vitro and in vivo studies on triclosan/PVM/MA copolymer/NaF combination as an anti-plaque agent," Am. J. Dent. 2:197-206.
QIU, 1997, Encyclopedia of Cosmetic Chemistry and Technology 1:114-174.

* cited by examiner

*Primary Examiner* — Dennis Heyer
(74) *Attorney, Agent, or Firm* — Rena Patel

(57) ABSTRACT

An oral composition exhibiting increased uptake by dental tissue of antibacterial compounds contained therein and eliminating or substantially reducing the discomfort and pain associated with dentinal hypersensitivity. The composition includes an orally acceptable vehicle for such composition, an effective therapeutic amount of an antibacterial compound, a mixture of anionic surfactant and amphoteric surfactant, the mixture having 0.1 wt. % to 2.0 wt. % anionic surfactant and 0.8 wt. % to 2.0 wt. % amphoteric surfactant, and a potassium ion releasable compound.

26 Claims, No Drawings

DENSENSITIZING DENTIFRICE EXHIBITING DENTAL TISSUE ANTIBACTERIAL AGENT UPTAKE

CROSS-REFERENCE TO RELATED APPLICATIONS

The present application is a national stage entry under 35 U.S.C. §371 of International Patent Application No. PCT/US2009/039194, filed Apr. 1, 2009, the entirety of which is hereby incorporated by reference.

BACKGROUND OF THE INVENTION

Dentinal hypersensitivity is defined as acute, localized tooth pain in response to physical stimulation as by thermal (hot or cold), osmotic, tactile, and/or a combination of thermal, osmotic and tactile stimulation of the exposed dentin.

It is known to the art that potassium salts are effective in the treatment of dentinal hypersensitivity. For example, the prior art discloses that toothpastes containing potassium salts, such as potassium nitrate, desensitize the teeth after tooth brushing for several weeks. It is reported that an elevation in the extracellular potassium concentration in the vicinity of pulpal nerves underlying sensitive dentin is responsible for the therapeutic desensitizing effect of topically applied oral products which contain potassium nitrate. Due to passive diffusion of potassium ion into and out of the open dentine tubules, repeated application of the active ingredient is necessary to build up the necessary concentration in the vicinity of the pulpal nerves.

In addition to treating dental hypersensitivity, it is desirable to provide dentifrice to control dental plaque. Plaque adheres tenaciously at the points of irregularity or discontinuity, e.g., on rough calculus surfaces, at the gum line and the like. Besides being unsightly, plaque is implicated in the occurrence of gingivitis and other forms of periodontal disease.

A wide variety of antibacterial agents have been suggested in the art to retard plaque formation and the oral infections and dental disease associated with plaque formation. For example, halogenated hydroxydiphenyl ether compounds such as triclosan are well known to the art for their antibacterial activity and have been used in oral compositions to counter plaque formation by bacterial accumulation in the oral cavity. The effectiveness of the antibacterial agent is dependent upon its delivery to and uptake by teeth and soft tissue areas of the gums.

There is therefore a need in the art to provide means whereby the delivery to and uptake by dental tissue of antibacterial compounds contained in oral compositions containing potassium ions to provide therapeutic efficacy of the antibacterial agent with a desensitizing dentifrice.

BRIEF SUMMARY OF THE INVENTION

In a first aspect, this invention provides an oral composition including an orally acceptable vehicle for such composition, an effective therapeutic amount of an antibacterial compound, a mixture of anionic surfactant and amphoteric surfactant, the mixture having 0.1 wt. % to 2.0 wt. % anionic surfactant based on the weight of the composition and 0.8 wt. % to 2.0 wt. % amphoteric surfactant based on the weight of the composition, and a potassium ion releasable compound. The composition exhibits increased uptake by dental tissue of antibacterial compounds contained therein and eliminates or substantially reduces the discomfort and pain associated with dentinal hypersensitivity.

In a second aspect, this invention provides a method for the treatment and prevention of bacterial plaque accumulation with reduced discomfort and pain associated with dentinal hypersensitivity comprising: administering to the oral cavity an oral composition comprising: an effective therapeutic amount of an antibacterial compound, a mixture of anionic surfactant and amphoteric surfactant, the mixture having 0.1 wt. % to 2.0 wt. % anionic surfactant based on the weight of the composition and 0.8 to 2.0 wt. % amphoteric surfactant based on the weight of the composition, and a potassium ion releasable compound.

In another aspect, this invention provides oral composition comprising an orally acceptable vehicle for such composition, an effective therapeutic amount of an antibacterial compound comprising a halogenated diphenyl ether, an effective therapeutic amount of an anti-hypersensitivity agent comprising a potassium salt, and a solubilizing agent for the antibacterial compound, the solubilizing agent comprising at least one of an ethoxylated sodium lauryl sulfate and a sodium cocoyl alkyl isethionate.

As will be demonstrated herein, the solubilizing agent, which may comprise the anionic/amphoteric surfactant mixture, results in uptake and bioavailability of the antibacterial agent which is unexpectedly higher for compositions having different surfactant compositions in the presence of potassium ion releasable compounds.

DETAILED DESCRIPTION OF THE INVENTION

The present invention provides for an oral composition including an orally acceptable vehicle for such composition, an effective therapeutic amount of an antibacterial compound, a mixture of anionic surfactant and amphoteric surfactant, and a potassium ion releasable compound. The composition exhibits increased uptake by dental tissue of antibacterial compounds contained therein and eliminates or substantially reduces the discomfort and pain associated with dentinal hypersensitivity.

The present invention also provides for an oral composition comprising an orally acceptable vehicle for such composition, an effective therapeutic amount of an antibacterial compound comprising a halogenated diphenyl ether, an effective therapeutic amount of an anti-hypersensitivity agent comprising a potassium salt, and a solubilizing agent for the antibacterial compound, the solubilizing agent comprising at least one of an ethoxylated sodium lauryl sulfate and a sodium cocoyl alk isethionate. The solubilizing agent has been found to overcome the problem of precipitation of halogenated diphenyl ether in the presence of potassium salt when using other surfactants, such as sodium lauryl sulfate.

The present invention is predicated on the finding by the present inventors that one or more surfactants that are tolerant to potassium salts can be employed in dentifrice compositions containing an anti-bacterial compound and, as an anti-hypersensitivity agent, a potassium salt, the surfactant(s) acting as a solubilizing agent for the anti-bacterial compound even in the presence of the potassium salt. By retaining the anti-bacterial compound in solution, so that it is not precipitated in the composition, the delivery and uptake of the anti-bacterial compound by teeth has been found by the inventors to be greatly enhanced.

The oral composition may contain a mixture of an anionic surfactant and an amphoteric surfactant. In one embodiment, the composition contains an anionic surfactant having a concentration ranging 0.1 wt. % to 2.0 wt. % based on the weight of the composition and/or an amphoteric surfactant having a concentration ranging 0.8 wt. % to 2.0 wt. % based on the weight of the composition. In another embodiment, the composition contains an anionic surfactant having a concentration ranging from 0.2 wt. % to 1.6 wt. % based on the weight of the composition and/or an amphoteric surfactant having a concentration ranging 0.9 to 1.8 wt based on the weight of the composition. In one embodiment, the anionic surfactant is sodium lauryl ethoxylated sulfate. In another embodiment, the sodium lauryl ethoxylated sulfate ("SLES") includes at least three ethoxylated groups. The ethoxylated sodium lauryl sulfate may be a mixture of ethoxylated sodium lauryl sulfates which has an average of three ethoxylate groups per molecule of ethoxylated sodium lauryl sulfate. In other embodiments, the amphoteric surfactant may be a sodium cocoyl alkyl isethionate, such as sodium cocoyl methyl isethionate ("Tauranol").

In the presence of potassium ions, the SLES/Tauranol surfactant mixture of one embodiment acts as a solubilizing agent for the antibacterial compound, in particular when the antibacterial compound comprises a halogenated diphenyl ether, such as 2,4,4'-trichloro-2'-hydroxy-diphenyl ether, so that the antibacterial compound remains in solution, which is essential for the effective delivery of the antibacterial compound. This is unlike certain oral compositions containing sodium laurel sulfate which causes the antibacterial compound to precipitate from solutions containing potassium ions.

Halogenated diphenyl ether antibacterial compounds that are useful for the preparation of the oral care compositions of the present invention, based on considerations of antiplaque effectiveness and safety, include 2,4,4'-trichloro-Z'-hydroxy-diphenyl ether (triclosan) and 2,2'-dihydroxy-5,5'-dibromo-diphenyl ether. In one embodiment, the antibacterial compound is 2,4,4'-trichloro-2'-hydroxy-diphenyl ether ("Triclosan").

Antibacterial compounds may also include phenol and its homologs, mono and polyalkyl and aromatic halophenols, resorcinol and its derivatives and bisphenolic compounds. Such phenolic compounds are fully disclosed in U.S. Pat. No. 5,368,844, the disclosure of which is incorporated herein by reference in its entirety. Phenolic compounds include n-hexyl resorcinol and 2,2'-methylene (4-chloro-6-bromophenol).

The halogenated diphenyl ether or phenolic antibacterial compound is present in the oral composition of the present invention in an effective therapeutic amount. In one embodiment, the effective therapeutic amount ranges of 0.05 wt. % to 2.0 wt. % based on the weight of the composition. In another embodiment, the effective therapeutic amount ranges of 0.1 wt. % to 1% wt. % based on the weight of the oral composition.

The source of desensitizing potassium ion is generally a water soluble potassium salt including potassium nitrate, potassium citrate, potassium chloride, potassium bicarbonate and potassium oxalate. In one embodiment, the water soluble potassium salt is potassium nitrate. In another embodiment, the water soluble potassium salt is potassium chloride. In such embodiment, the potassium salt is generally incorporated in one or more of the dentifrice components at a concentration ranging of 0.5 wt. % to 20 wt. % based on the weight of the composition. In another such embodiment, the potassium salt is generally incorporated in one or more of the dentifrice components at a concentration ranging of 3 wt. % to 15 wt. % based on the weight of the composition.

In the preparation of an oral composition in accordance with the practice of the present invention, an orally acceptable vehicle including a water-phase with humectant is present. The humectant includes one or more of glycerin, sorbitol, propylene glycol and mixtures thereof. In one embodiment, water is present in amount of at least 10 wt. % based on the weight of the composition. In another embodiment, water is present in an amount of at least 30 wt. % to 60 wt. % based on the weight of the composition. In yet another embodiment, the humectant concentration typically totals 40-60 wt. % of the oral composition.

Dentifrice compositions such as toothpastes and gels also typically contain polishing materials. In one embodiment, the polishing material includes crystalline silica, having a particle size of up to 20 microns, such as commercially available Zeodent 115, or Zeodent 165, silica gel or colloidal silica. In another embodiment, the polishing material includes compositions such as complex amorphous alkali metal aluminosilicates, hydrated alumina, sodium metaphosphate, sodium bicarbonate, calcium carbonate, calcium pyrophosphate, dicalcium phosphate and dicalcium phosphate dihydrate. In one embodiment, the polishing material is included in semi-solid or pasty dentifrice compositions, of the present invention, in an amount of 15 wt. % to 60 wt. %. In another embodiment, the composition of the present invention includes polishing material having concentrations ranging of 20 wt. % to 55 wt. % based on the weight of the composition.

Dentifrices prepared in accordance with the present invention typically contain a natural or synthetic thickener. Suitable thickeners include Irish moss, i-carrageenan, gum tragacanth, starch, polyvinylpyrrolidone, hydroxyethypropyl cellulose, hydroxybutyl methyl cellulose, hydroxypropyl methylcellulose, hydroxyethyl cellulose, sodium carboxymethyl cellulose sodium CMC) and colloidal silica. In one embodiment, the thickener concentration ranges of 0.1 wt. % to 5 wt. % based on the weight of the composition. In another embodiment, the thickener concentration ranges of 0.5 wt. % to 2 wt. %, based on the weight of the composition.

The oral composition may also contain a source of fluoride ions, or fluoride-providing compound, as an anti-caries agent. In one embodiment, the fluoride ion composition is provided in an amount sufficient to supply fluoride ions ranging from 25 ppm to 5,000 ppm of the oral composition. In another embodiment, the fluoride ion composition is provided in an amount sufficient to supply fluoride ions ranging from 500 to 1500 ppm of the oral composition. Representative fluoride ion providing compounds include inorganic fluoride salts, such as soluble alkali metal salts, for example, sodium fluoride, potassium fluoride, sodium fluorosilicate, ammonium fluorosilicate and sodium monofluorphosphate, as well as tin fluorides, such as stannous fluoride and stannous chloride.

An antibacterial enhancing agent may also be included in the oral composition. In one embodiment, the antibacterial enhancing agent is incorporated in the compositions of the present invention in weight amounts ranging of 0.05 wt. % to 3 wt. % based on the weight of the composition. In another embodiment, the antibacterial enhancing agent is incorporated in the compositions of the present invention in weight amounts ranging of 0.1 wt. % to 2 wt. % based on the weight of the composition.

The use of antibacterial enhancing agents in combination with antibacterial agents such as triclosan is known to the art, as for example U.S. Pat. No. 5,188,821 and U.S. Pat. No. 5,192,531, each of which are incorporated by reference herein it its entirety. In one embodiment, the antibacterial enhancing agent is an anionic polymeric polycarboxylate having a molecular weight ranging from 1,000 to 1,000,000 g/mole. In another embodiment, the antibacterial enhancing agent is an anionic polymeric polycarboxylate having a molecular weight ranging from 30,000 to 500,000 g/mole. In one embodiment, the anionic polymeric polycarboxylates are generally employed in the form of their free acids. In another embodiment, the anionic polymer polycarboxylates are employed in the form of a partially or fully neutralized water soluble alkali metal salt, e.g., sodium, potassium or ammonium salts. In one embodiment, the antibacterial enhancing agents include 1:4 to 4:1 copolymers of maleic anhydride or add with another polymerizable ethylenically unsaturated monomer. In one such embodiment, the maleic anhydride copolymer includes a methyl vinyl ether/maleic anhydride copolymer having a molecular weight ("M.W.") ranging from 30,000 to abut 1,000,000 g/mole. In another such embodiment, the maleic anhydride copolymer includes a methyl vinyl ether/maleic anhydride copolymer having a molecular weight ranging from 30,000 to 500,000 g/mole. These copolymers are commercially available, for example, under the trademark Gantrez, including Gantrez AN 139 (M.W. 500,000 g/mole), AN 119 (M.W. 250,000 g/mole); and Gantrez S-97 Pharmaceutical Grade (M.W. 700,000 g/mole), of GAF Corporation.

Any suitable flavoring or sweetening material may also be employed in the preparation of the oral compositions of the present invention. Examples of suitable flavoring constituents include flavoring oils, e.g. oil of spearmint, peppermint, wintergreen, clove, sage, eucalyptus, marjoram, cinnamon, lemon, orange, and methyl salicylate. Suitable sweetening agents include sucrose, lactose, maltose, xylitol, sodium cyclamate, aspartyl phenyl alanine methyl ester, saccharine and the like. Suitably, flavor and sweetening agents may each or together constitute 0.1 wt. % to 5 wt. %, of the oral composition.

Various other materials may be incorporated in the oral preparations of this invention such as whitening agents, including urea peroxide, calcium peroxide, and hydrogen peroxide, preservatives, vitamins such as vitamin B6, B12, E and K, silicones, chlorophyll compounds and potassium salts for the treatment of dental hypersensitivity such as potassium nitrate and potassium citrate. These agents, when present, are incorporated in the compositions of the present invention in amounts which do not substantially adversely affect the properties and characteristics desired.

The present invention also provides for a method for the treatment and prevention of bacterial plaque accumulation with reduces discomfort and pain associated with dentinal hypersensitivity by administering to the oral cavity the oral composition discussed herein.

The manufacture of the oral composition of the present invention is accomplished by any of the various standard techniques for producing such compositions. To make a dentifrice, a vehicle is prepared containing humectant, for example, one or more of glycerin, glycerol, sorbitol, and propylene glycol, thickener agents and antibacterial agent such as triclosan, and the vehicle and a mixture of anionic and amphoteric surfactants are added, followed by blending in of a polishing agent, as well as fluoride salts, with the pre-mix. Finally, flavoring agent, is admixed and the pH is adjusted to between 6.8 to 7.0.

The following examples are further illustrative of the present invention, but it is understood that the invention is not limited thereto. All amounts and proportions referred to herein and in the appended claims are by weight, unless otherwise indicated.

EXPERIMENTAL EXAMPLES

Examples 1 and 2

Compositions

Examples 1 and 2 were prepared as described above and have the compositions as described in Table 1.

TABLE 1

| INGREDIENT | Example 1 | Example 2 |
|---|---|---|
| GLYCERIN | 10.00 | 10.00 |
| sodium CMC | 2.40 | 2.40 |
| Carregeenan PS223 | 0.90 | 0.90 |
| SACCHARIN SODIUM | 0.30 | 0.30 |
| SODIUM FLUORIDE | 0.24 | 0.24 |
| TITANIUM DIOXIDE | 0.50 | 0.50 |
| GANTREZ liquid (15%) | 15.00 | — |
| SODIUM HYDROXIDE 50% | 1.20 | 1.20 |
| ZEODENT - 165 | 1.50 | 1.50 |
| ZEODENT - 115 | 11.00 | 11.00 |
| TRICLOSAN | 0.30 | 0.30 |
| SLES (68% liquid) | 1.55 | 0.31 |
| TAURANOL (95% solid) | 0.98 | 1.76 |
| POTASSIUM CHLORIDE | 3.75 | 3.75 |
| FLAVOR | 1.00 | 1.00 |
| CP PURIFIED WATER | 49.38 | 64.84 |
| TOTAL | 100.00 | 100.00 |

The effect of a mixture of anionic and amphoteric surfactants, when present in an oral composition having a potassium releasable ion compound, on the uptake absorption of a halogenated diphenyl ether antibacterial agent to dental tissue was assessed. The uptake was assessed using disks of saliva coated hydroxyapatite (SCHAP), the mineral phase of dental enamel, as an in vitro experimental model for human teeth. The in vitro assessment has been found to correlate to in vivo uptake of antibacterial agents on dental tissue surfaces.

In this in vitro assessment, hydroxyapatite (HAP) is washed extensively with distilled water, collected by vacuum filtration, and dried overnight at 37° C. The dried HAP is ground into a powder and 150 milligrams (mgs) of the powder is placed into a chamber of a KBr pellet die (Barnes Analytical, Stanford, Conn.). The HAP powder is compressed for 6 minutes at 10,000 pound in a Carver Laboratory press to prepare 13 mm diameter disks which are sintered for 4 hours at 800° C. in a Thermolyne furnace.

Stimulated saliva was clarified by centrifuging for 10 minutes at 15,000×g. Hydroxyapatite disks were incubated in the clarified saliva overnight in a 37° C. shaking water bath to develop a pellicle.

To determine the delivery of triclosan to a saliva treated hydroxyapatite disk (SCHAP) disk, SCHAP disks were treated with a dentifrice slurry prepared using ingredients from compositions identified in Table I. The amounts of dentifrice slurry used to contact the disks simulated in vivo surface to volume ratios found in the mouth. The dentifrice slurries were a liquid phase solution which contained all the components of a dentifrice except the abrasive. The liquid phase, in part, simulates brushing condition. After incubation for 30 minutes at 37° C., the SCHAP disks were removed from the dentifrice slurry, washed three times with water.

The uptake absorption of Trielosan, on SCHAP disks from the compositions of Table 1 are set forth in Table 2 below. In Table 2 the Comparative Example comprised a commercially available toothpaste containing triclosan having sodium lauryl sulfate as the surfactant but without a potassium salt additive acting as an anti-hypersensitivity agent, and in particular a toothpaste sold by the present Assignee Colgate-Palmolive Company under the trade mark Total Clean Mint.

TABLE 2

| Sample | Triclosan Uptake ppm |
| --- | --- |
| Example 1 | 36 |
| Example 2 | 32 |
| Comparative Example | 20 |

The results in Table 2 demonstrate that the inventive oral composition examples, uptake 60-80% greater amount of triclosan compared to the comparative oral formulation having sodium lauryl sulfate as the surfactant even with the addition to the inventive oral composition examples of a potassium salt additive acting as an anti-hypersensitivity agent, which would have been expected to cause precipitation of triclosan, and consequently reduced triclosan uptake.

Example 3

Inhibition of Bacterial Growth

An inhibition of bacterial growth study was performed to demonstrate the adsorption of the antibacterial agent of a dentifrice of the present invention onto SCHAP disks and the resulting inhibition of bacterial growth using such disks. SCHAP (hydroxyapatite) disks which were saliva coated (after overnight incubation with clarified saliva at 37° (–) were incubated at 37° C. for 30 minutes with 1 ml supernatant of 1:1 slurry of a dentifrice of the present invention, in particular the compositions of Examples 1 and 2. For comparison, the test was also carried out on the dentifrice of the Comparative Example and on water. After the incubation, the dentifrice was aspirated; the disks were transferred into a falcon tube; washed three times with 5 ml water; vertexed; and aspirated. The disks were then inoculated with 10 ml bacterial suspension containing *Actinomyces viscosus*, a bacterium associated with dental caries, at a concentration of 0.5 OD (Optical Density) at 610 nm. The growth of bacteria was then measured after 24 hours in terms of OD, wherein the lower the OD, the lower the presence of bacteria, i.e. the lower the growth of bacteria. The mean OD result obtained is recorded in Table 3.

TABLE 3

| Sample | OD at 610 nm |
| --- | --- |
| Water | 1.8 |
| Example 1 | 0.7 |
| Example 2 | 0.7 |
| Comparative Example | 0.6 |

The results in Table 3 show that the inventive oral compositions provide effective bacterial grown inhibition compared to the comparative oral formulation having triclosan, sodium lauryl sulfate as the surfactant and without a potassium ion source as an anti-hypersensitivity agent.

We claim:

1. An oral composition comprising:
  an orally acceptable vehicle,
  an effective therapeutic amount of an antibacterial compound,
  a mixture of anionic surfactant and sodium cocoyl methyl isethionate, wherein the mixture having 0.1 wt. % to 2.0 wt. % anionic surfactant based on the weight of the composition and 0.8 wt. % to 2.0 wt. % sodium cocoyl methyl isethionate based on the weight of the composition, and
  a potassium ion releasable compound,
  wherein
  the anionic surfactant is sodium lauryl ethoxylated sulfate including at least three ethoxylate groups.

2. The oral composition of claim 1, wherein said antibacterial compound comprises a halogenated diphenyl ether.

3. The oral composition of claim 2, wherein the halogenated diphenyl ether comprises 2,4,4'-trichloro-2'-hydroxy-diphenyl ether.

4. The oral composition of claim 3, wherein the 2,4,4'-trichloro-2'-hydroxy-diphenyl ether is present in the composition at a concentration of 0.05 wt. % to 2.0 wt. % based on the weight of the composition.

5. The oral composition of claim 1 wherein the potassium ion releasable compound is a water soluble potassium salt.

6. The oral composition of claim 5, wherein the potassium ion releasable compound is potassium chloride.

7. The oral composition of claim 5, wherein the potassium ion releasable compound is potassium nitrate.

8. The oral composition of claim 1, wherein the surfactant mixture increases dental tissue uptake of the antibacterial compounds contained in the oral composition.

9. The oral composition of claim 1, wherein the composition eliminates or substantially reduces the discomfort and pain associated with dentinal hypersensitivity.

10. A method for the treatment and prevention of bacterial plaque accumulation with reduced discomfort and pain associated with dentinal hypersensitivity comprising:
  administering to the oral cavity an oral composition comprising:
    an effective therapeutic amount of an antibacterial compound,
    a mixture of anionic surfactant and sodium cocoyl methyl isethionate, the mixture having 0.1 wt. % to 2.0 wt. % anionic surfactant based on the weight of the composition and 0.8 to 2.0 wt. % sodium cocoyl methyl isethionate based on the weight of the composition, and
    a potassium ion releasable compound,
    wherein the anionic surfactant is sodium lauryl ethoxylated sulfate including at least three ethoxylate groups.

11. The method of claim 10, wherein said antibacterial compound comprises a halogenated diphenyl ether.

12. The method of claim 11, wherein the halogenated diphenyl ether comprises 2,4,4'-trichloro-2'-hydroxy-diphenyl ether.

13. The method of claim 12, wherein the 2,4,4'-trichloro-2'-hydroxydiphenyl ether is present in the composition at a concentration of 0.05 wt. % to 2.0 wt. % based on the weight of the composition.

14. The method of claim 10, wherein the potassium ion releasable compound is a water soluble potassium salt.

15. The method of claim 14, wherein the potassium ion releasable compound is potassium chloride.

16. The method of claim 14, wherein the potassium ion releasable compound is potassium nitrate.

17. An oral composition comprising
  an orally acceptable vehicle for such composition,
  an effective therapeutic amount of an antibacterial compound comprising
    a halogenated diphenyl ether,
  an effective therapeutic amount of an anti-hypersensitivity agent comprising a potassium salt, and
a solubilizing agent for the antibacterial compound,
wherein the solubilizing agent comprising at least one of an ethoxylated sodium lauryl sulfate and a sodium cocoyl alkyl isethionate,
wherein the ethoxylated sodium lauryl sulfate is a mixture of ethoxylated sodium lauryl sulfates which has an average of three ethoxylate groups per molecule of ethoxylated sodium lauryl sulfate.

18. The oral composition of claim 17, wherein the solubilizing agent comprises a mixture of the ethoxylated sodium lauryl sulfate and the sodium cocoyl alkyl isethionate.

19. The oral composition of claim 17, wherein the halogenated diphenyl ether comprises 2,4,4'-trichloro-2'-hydroxydiphenyl ether.

20. The oral composition of claim 19, wherein the 2,4,4'-trichloro-2'-hydroxydiphenyl ether is present in the composition at a concentration of 0.05 wt. % to 2.0 wt. % based on the weight of the composition.

21. The oral composition of claim 17, wherein the potassium salt is water soluble.

22. The oral composition of claim 21, wherein the potassium salt is at least one of potassium chloride and potassium nitrate.

23. The oral composition of claim 17, wherein the sodium cocoyl alkyl isethionate is sodium cocoyl methyl isethionate.

24. The oral composition of claim 17, wherein the solubilizing agent comprises 0.1 wt. % to 2.0 wt. %, based on the weight of the composition, of the ethoxylated sodium lauryl sulfate.

25. The oral composition of claim 17, wherein the solubilizing agent comprises 0.8 wt. % to 2.0 wt. %, based on the weight of the composition, of the sodium cocoyl alkyl isethionate.

26. A method for the treatment and prevention of bacterial plaque accumulation with reduced discomfort and pain associated with dentinal hypersensitivity comprising administering to the oral cavity an oral composition according to claim 17.

* * * * *